(12) United States Patent
Peterson et al.

(10) Patent No.: US 6,617,760 B1
(45) Date of Patent: Sep. 9, 2003

(54) ULTRASONIC RESONATOR

(75) Inventors: Thomas Peterson, Erie, PA (US); Dhamendra Pal, Erie, PA (US)

(73) Assignee: Cybersonics, Inc., Erie, PA (US)

( * ) Notice: Subject to any disclaimer, the term of this patent is extended or adjusted under 35 U.S.C. 154(b) by 0 days.

(21) Appl. No.: 09/518,801

(22) Filed: Mar. 3, 2000

Related U.S. Application Data (60) Provisional application No. 60/123,041, filed on Mar. 5, 1999.

(51) Int. Cl.⁷ .............................................. H01L 41/08
(52) U.S. Cl. .............. 310/328; 310/323.18; 310/323.19
(58) Field of Search ................................ 310/328, 330, 310/331, 323.18, 323.19; 331/154

(56) References Cited

U.S. PATENT DOCUMENTS

| | | | |
|---|---|---|---|
| 3,027,690 A | * 4/1962 | Roney ........................... 310/26 |
| 3,381,525 A | * 5/1968 | Kartluke et al. ............... 310/26 |
| 3,546,498 A | * 12/1970 | McMaster et al. ..... 310/323.19 |
| 3,591,862 A | 7/1971 | Winston ....................... 310/8.2 |
| 3,830,240 A | 8/1974 | Antonevich ................ 128/24 A |
| 3,861,391 A | * 1/1975 | Antonevich et al. ............. 601/4 |
| 3,957,252 A | 5/1976 | Storz .......................... 366/118 |
| 3,985,344 A | 10/1976 | McCord ...................... 366/127 |
| 4,064,886 A | 12/1977 | Heckele ...................... 134/95.3 |
| 4,486,680 A | * 12/1984 | Bonnet et al. .......... 310/323.19 |
| 4,537,511 A | * 8/1985 | Frei ............................... 134/1 |
| 4,572,184 A | * 2/1986 | Stohl et al. ............. 310/323.19 |
| 4,589,403 A | 5/1986 | Ouchi et al. ................. 600/104 |
| 4,602,184 A | * 7/1986 | Meitzler ....................... 310/322 |
| 4,741,731 A | * 5/1988 | Starck et al. ........... 310/323.18 |
| 4,870,953 A | 10/1989 | DonMichael et al. ........ 606/128 |
| 4,920,954 A | * 5/1990 | Alliger et al. ............... 606/128 |
| 5,112,300 A | * 5/1992 | Ureche ................... 310/323.18 |
| 5,156,143 A | 10/1992 | Bocquet et al. ................ 128/24 |
| 5,240,675 A | 8/1993 | Wilk et al. ...................... 422/22 |
| 5,270,484 A | * 12/1993 | Tsuchiya et al. ........ 310/323.01 |
| 5,289,436 A | * 2/1994 | Terhune ....................... 181/400 |
| 5,304,115 A | 4/1994 | Pflueger et al. ................ 604/22 |
| 5,337,730 A | 8/1994 | Maguire ...................... 600/157 |
| 5,375,589 A | 12/1994 | Bhatta ......................... 600/104 |
| 5,397,293 A | * 3/1995 | Alliger et al. .................. 601/2 |
| 5,462,604 A | 10/1995 | Shibano et al. ................. 134/1 |
| 5,630,795 A | 5/1997 | Kuramoto et al. ............ 604/30 |
| 5,830,127 A | * 11/1998 | DeCastro ..................... 600/157 |
| 6,140,744 A | * 10/2000 | Bran ...................... 310/323.19 |
| 6,450,975 B1 | * 9/2002 | Brennan et al. ............. 600/585 |

FOREIGN PATENT DOCUMENTS

| | | | |
|---|---|---|---|
| DE | 4041365 A1 | 7/1992 | |
| GB | 1199937 | 7/1970 | ..................... 23/27 |

* cited by examiner

*Primary Examiner*—Thomas M. Dougherty
(74) *Attorney, Agent, or Firm*—The Bilicki Law Firm, P.C.

(57) ABSTRACT

An ultrasonic resonator comprising a wire member with an elongated shaft having a proximal end and a distal end, the proximal end further including a filler material disposed within the proximal end; a crimp screw with an annular end and a threaded end, the annular end adapted to receive and fixedly secure the proximal end of the wire member, the annular end being crimped after the proximal end of the wire member is inserted within the annular end of the crimp screw; an ultrasonic transducer adapted to receive the threaded end of the crimp screw; and the ultrasonic transducer operatively connected to an ultrasonic generator.

53 Claims, 10 Drawing Sheets

ULTRASONIC RESONATOR

CROSS REFERENCES

This application is a continuation of and claims priority to provisional application No. 60/123,041, filed on Mar. 5, 1999, entitled "Method and Apparatus for Cleaning Medical Instruments and the Like."

FIELD OF THE INVENTION

This invention relates generally to an apparatus for producing transverse and longitudinal ultrasonic vibrations along an elongated wire. More particularly, the is invention relates to an apparatus that can be used for cleaning interior channels of medical devices such as brain shunts and endoscopes, extracting pacemaker leads and other leads in a human body, cleaning investment castings, treating atherosclerotic plaque and thromboses, coring, and drilling.

DETAILED DESCRIPTION OF EMBODIMENTS OF THE INVENTION

One characteristic of one embodiment of the present invention is the ability of the wire resonator to generate both transverse and longitudinal ultrasonic vibrations simultaneously. At its proximal end, the resonator is coupled to an ultrasonic transducer and produces substantial transverse vibrations at positions along its entire length, as well as longitudinal vibrations at its distal end. The transducer of one embodiment of the invention is comprised of a plurality of ceramic elements that are stacked one on the other with metal separators between the ceramic elements such that one end of the ceramic elements will touch the horn and the other end of the plurality of ceramic elements is attached to a bias bolt. The electrical wires that transport energy from the generator to the transducer are connected to these metal separators to excite the molecules within the ceramic elements. The bias bolt is screwed into the plurality of ceramic elements and compresses the ceramic elements against the horn. In one embodiment, the ceramic elements are PZT 8 or PZT 4 ceramic elements and are arranged such that the polarity of each of the ceramic elements is aligned with the others. In another embodiment, the transducer is comprised of four PZT 8 ceramic elements. Within the liquid-filled lumen of an instrument to be cleaned, the combination of transverse and longitudinal ultrasonic wave motion causes a turbulence that results in cavitational cleaning action in the liquid. If the device is not placed within a liquid-filled lumen, the transverse and longitudinal waves emanate from the distal tip of the wire resonator and act to break up the material against which the wire resonator is abutting.

The transverse vibrations, which occur at antinode positions along the length of the wire resonator, generate cavitational cleaning action in the liquid at each position. As a result, cavitational cleaning action occurs simultaneously at a multiplicity of sites within the interior channel or lumen of the instrument. The cavitational action in the channel of the instrument facilitates and accelerates the detachment of contaminants such as particles embedded or trapped in crevasses and corners.

During a typical ultrasonic cleaning process, liquid is passed through the lumen or channel being cleaned. In this cleaning procedure, transverse and longitudinal ultrasonic vibrations are produced by the resonator within the lumen or channel to be cleaned, while a liquid, for example, an aqueous solution of a suitable sterilant, disinfectant, and/or cleaning agent, is passed through an irrigation port into the proximal end of the lumen and allowed to pass out through the distal end.

In the operation of the transducer, a pulsed mode may be preferred to continuous wave mode. In the pulsed mode (e.g. 50% on; 50% off) the cleaning fluid is degassed very quickly and increases the effects of ultrasonic cavitation.

The resonator can be a solid or annular rod-like or wire member composed of a metallic material capable of producing both transverse and longitudinal ultrasonic waves in response to the action of an ultrasonic transducer. Materials for this purpose include metals or alloys such as nickel or nickel cobalt alloys characterized by a high modulus of elasticity or materials that can be treated, such as by cold-working and/or heat treatment, to achieve a high modulus of elasticity, preferably greater than 18 million psi. Such materials are more readily excited into transverse ultrasonic motion at lower stress levels, thus reducing the energy necessary to produce transverse motion in titanium alloys.

At lower power levels, less heat is generated, thus reducing heating of the ultrasonic resonator and increasing the resonator life. Especially useful for this purpose are alloys of nickel/cobalt/chrome/molybdenum such as MP-35N alloy or Elgiloy. One such material is Elgiloy wire (a cobalt alloy containing about 0.15% C, 20.0% Cr, 15.0% Ni, 15.0% Fe, 7.0% Mo and 0.04% Be) that has been 48% cold reduced and heat treated at 980 degrees Fahrenheit for approximately five hours. The wire resonator may be flexible or rigid. The modulus of elasticity, endurance limit, and tensile strength of Elgiloy and other example materials can be seen in the following

TABLE 1

| Alloy | Modulus of Elasticity (EO\) × $10^6$ PSI | Endurance Limit × $10^3$ PSI | Tensile Strength × $10^3$ PSI |
|---|---|---|---|
| Ti (6L-4V) | 15–17 | 60–85 | 130 |
| Stainless Steel | 28 | 39 | 85–90 |
| Elgiloy | 29.5 | NA | 230–250 |

An alternate embodiment of the resonator of the present invention includes the use of a plastic that can approximate the characteristics of the above listed metal alloys. Generally, the diameter of the rod or wire that constitutes the resonator is typically between about 0.010 and about 0.100 inches, and typically between about 0.015 and about 0.060 inches in diameter. To provide an even higher degree of flexibility, for applications where the resonator must be inserted in, and conform to the shape of, a tightly coiled medical instrument, the wire diameter is commonly in the range of about 0.025 to about 0.035 inches.

The length of the metal wire resonator may vary but is generally greater than the length of the channel to be cleaned and is advantageously a multiple of the wave length of the driving frequency of the ultrasonic generator and selected as necessary to terminate at the distal end of the resonator at a longitudinal antinode position.

The operating frequency may vary considerably, but will typically be in the range of about 15,000 to about 100,000 Hz. In general, the lower the frequency, the stronger the cavitation action, the more thorough the cleaning action, and the greater the chance for cavitation damage to the instrument being cleaned. The higher the frequency, the weaker the cavitation action, but the less potential for cavitation damage to the instrument being cleaned. An example operating frequency is about 20,000 Hz for a solid flexible resonator made of Elgiloy, 15 inches long, and 0.035 inches diameter. Of course, other operating frequencies can be used. The lengths are proportioned as necessary such that the distal end of the resonator is at a longitudinal motion antinode position. At 20,000 Hz a solid 0.035 inch diameter wire produces concentric transverse motion at intervals of about every 0.5 inches along the length of the resonator. For a 15 inch long resonator, 25 transverse antinode positions are produced. Using the same wire length and driving frequency, but with a wire diameter of 0.020 inches, concentric transverse wave motion is produced at intervals of about 0.325 inches along the entire length of the resonator. Approximately 46 transverse antinode positions are produced.

The transverse half wave lengths of a fixed free bar, such as a wire resonator attached at one end to a transducer, can be determined theoretically by the following equation:

$$\frac{1}{2}\lambda = [(C_n C_c d/2)/2F] * \frac{1}{2}[1/(n-1)]$$

where $C_n$ (boundary condition)=$[(2n-21)/8]\pi$ wherein n=½λ; where $\lambda = C_c/F$; n=bar length; $C_c$=bar velocity; d=diameter; and F=driving frequency.

The wire resonator, either solid of annular, is attached at its proximal end to a transducer. The attachment is made by means of a crimp screw that is threaded on one end (to be screwed into a threaded hole in the transducer) and provided with a hole in the other end into which the proximal end of the wire resonator is inserted. If the wire resonator is solid, a hole must first be bored into the proximal end, leaving a ring of metal from the wire resonator encircling the hole. The hole does not typically extend more than approximately 0.1 inches from the edge of the proximal end. In this embodiment, the hole in the solid wire is formed by an electro-deposition materials (edm) process wherein tiny holes can be bored into tiny areas. The radius of one of the wires described herein is typically approximately 0.0360 to approximately 0.0370 inches. The holes that are bored through the edm process must necessarily be smaller than the radius of the wire. If the annular wire resonator is utilized, no hole need be drilled into the annular resonator since the annular resonator is hollow, unless a hole of a larger diameter is required.

Before insertion into the crimp screw, the hole of the solid wire or the hollow portion of the annular wire is partially filled with a metal filler compound, such as piano wire or the like. The proximal end of the wire resonator is then inserted into the end of the crimp screw. The end of the crimp screw into which the wire is inserted is then crimped around the wire to provide a tight pressure attachment. The combination of the crimping process and the motion of the wire resonator, in a non-filled resonator, places too much pressure on the joint of the wire resonator at the point of coupling to the crimp screw because the wire is deformed at that juncture. Non-filled wire resonators tend to fail or crack at that juncture because of the pressure on the joint. However, with the insertion of the metal filler compound, the pressure on the joint is lessened and the wire resonator then has a longer life span and a reduced risk of failure. This attachment device produces a mismatch boundary condition that reduces the longitudinal motion and promotes transverse wave generation.

In an alternate embodiment, the apparatus comprises a multiplicity of wire resonators attached to the transducer. In another third alternate embodiment, the wire resonator is comprised of an annular metal wire resonator that is coupled to the ultrasonic transducer through the use of a crimp screw as well. Alternately, the annular wire resonator is partially filled with a metal filler compound such as piano wire or the like, then inserted into the crimp screw. The end of the crimp screw into which the annular wire is inserted is then crimped around the wire to provide a tight pressure attachment.

In another embodiment of the present invention, a capturing member is integral with and surrounds the solid or annular wire resonator that is to be inserted into the ultrasonic transducer horn. The capturing member is crimped to the wire resonator. The capturing member is fixedly attached to the wire resonator at a position that allows a portion of the wire resonator to fit within the transducer horn. The wire resonator is inserted into the ultrasonic transducer horn. A barrier member, shaped like a box in this embodiment, possesses a hole in one end for allowing the wire resonator to be sheathed in the hole. The barrier member slides over the wire resonator and the area where the resonator is coupled to the ultrasonic transducer and is fixedly attached to the ultrasonic transducer horn. The hole in the barrier member of this embodiment must be smaller in diameter than the combined diameter of the capturing member and wire resonator; yet, larger than the diameter of the wire resonator only. With this arrangement, the capturing member is located between the edge of the ultrasonic transducer horn and the inside edge of the barrier member. When the ultrasonic transducer is activated, the wire resonator moves back and forth in a limited range of motion, i.e., from when the capturing member abuts the edge of the transducer horn to where the capturing member abuts the edge of the barrier member. The wire resonator will move back and forth very quickly. The transverse motion induces the wire resonator to act like a small jackhammer and increases the power output of the resonator. In this embodiment, the wire resonator and ultrasonic transducer do not generate the typical amounts of heat that is generated when the wire resonator is fixedly secured to the ultrasonic transducer.

The wire, made of Elgiloy, for example, further include a protective coating which may be a hard coating, such as titanium nitride, or a soft coating such as polytetrafluoroethylene (e.g., Teflon; fluon; etc.) or the like to protect it from damage due to the cavitational action of the liquid. Hard coatings such as titanium nitride minimize the attenuation of the ultrasonic energy.

Referring now to the drawings in detail, for the ease of the reader, like reference numerals designate identical or corresponding parts throughout the views depicted in the drawings. It should be noted that each embodiment is not depicted by a drawing nor are each of the notable applications depicted by a drawing. It should also be noted that wherever a solid resonator appears in one of the drawings, an annular resonator may be substituted, and vice versa.

Figure 1:
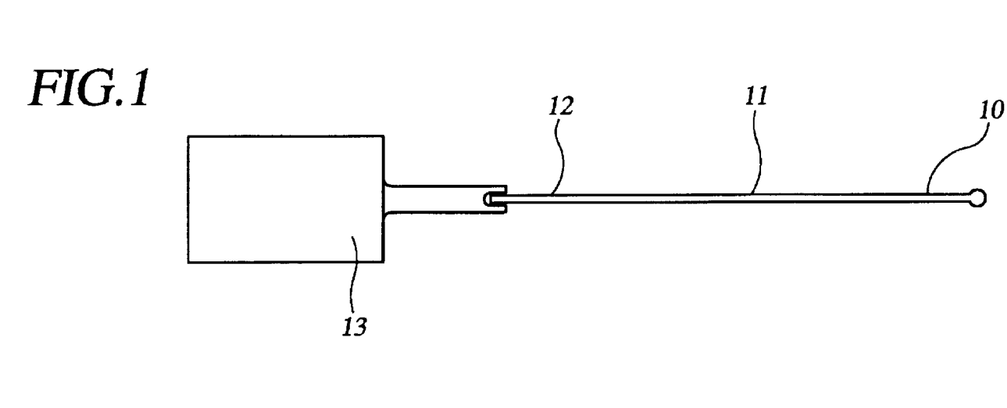
FIG. 1 is a longitudinal sectional view of an ultrasonic resonator coupled at its proximal end to an ultrasonic generator.
Figure 13:
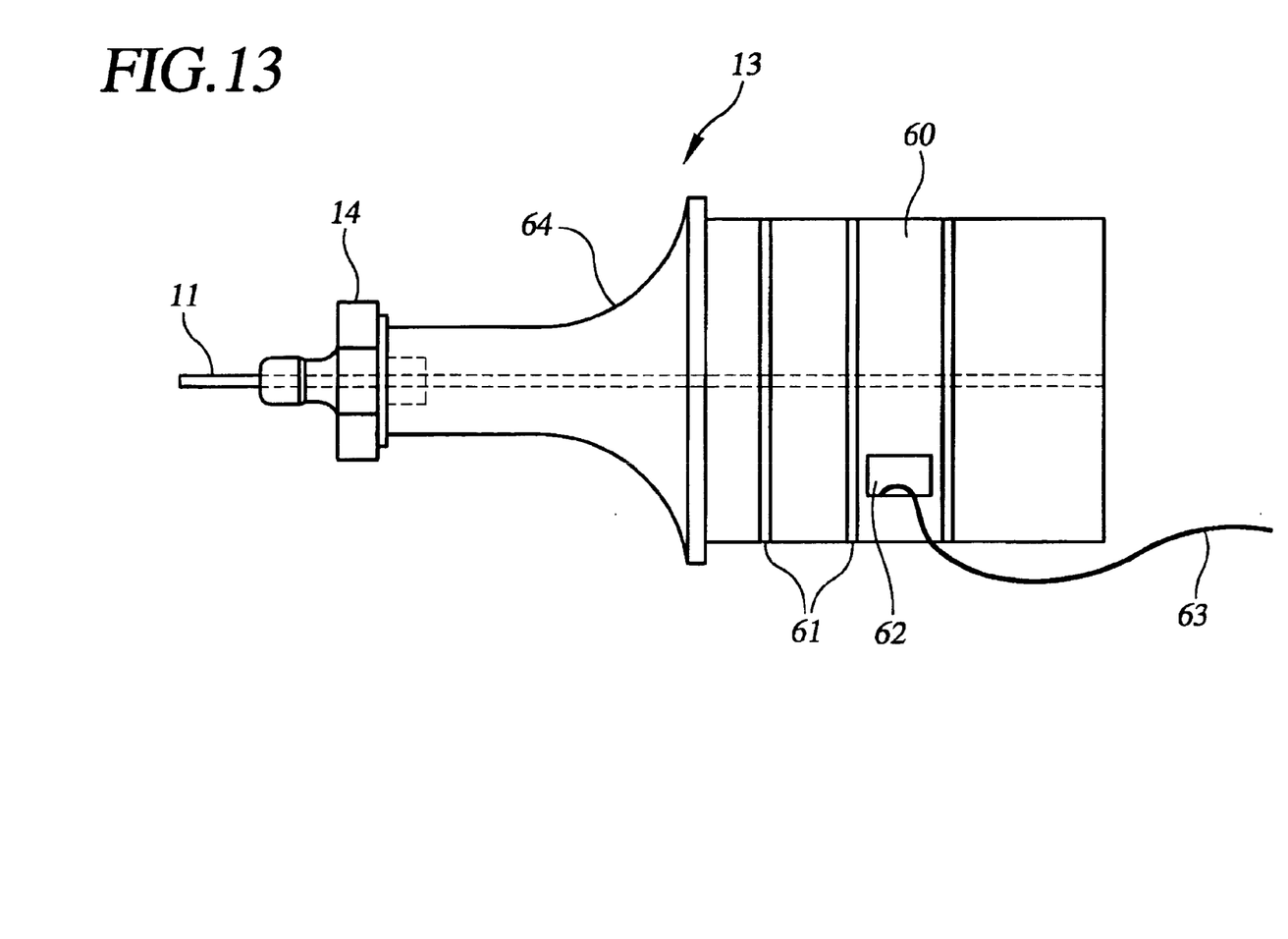
FIG. 13 is a longitudinal detailed view of the ultrasonic transducer that may be utilized with any of the embodiments of the invention described herein.

In FIG. 1, ultrasonic resonator (11) is shown with distal end (10) and attached at its proximal end (12) to an ultrasonic transducer (13). The ultrasonic resonator (11) is a solid resonator of a material capable of producing both transverse and longitudinal vibrations in response to ultrasonic transducer (13). The material may be of the magnetorestrictive type or of the piezoelectric type. One embodiment of the ultrasonic transducer (13) is depicted in FIG. 13. The ultrasonic transducer (13) in FIG. 13 possesses a plurality of piezoelectric ceramic elements (60) stacked one on the other with metal separators (61) between the ceramic elements (60) such that one end of the ceramic elements (60) touches the horn (64) and the other end of the plurality of ceramic elements (60) is attached to a bias bolt (not shown). The electrical wires (63) that transport energy from the generator (not shown) to the transducer (13) are connected to these metal separators (61) via metal connectors (62) to excite the molecules within the ceramic elements (13).

Figure 2:
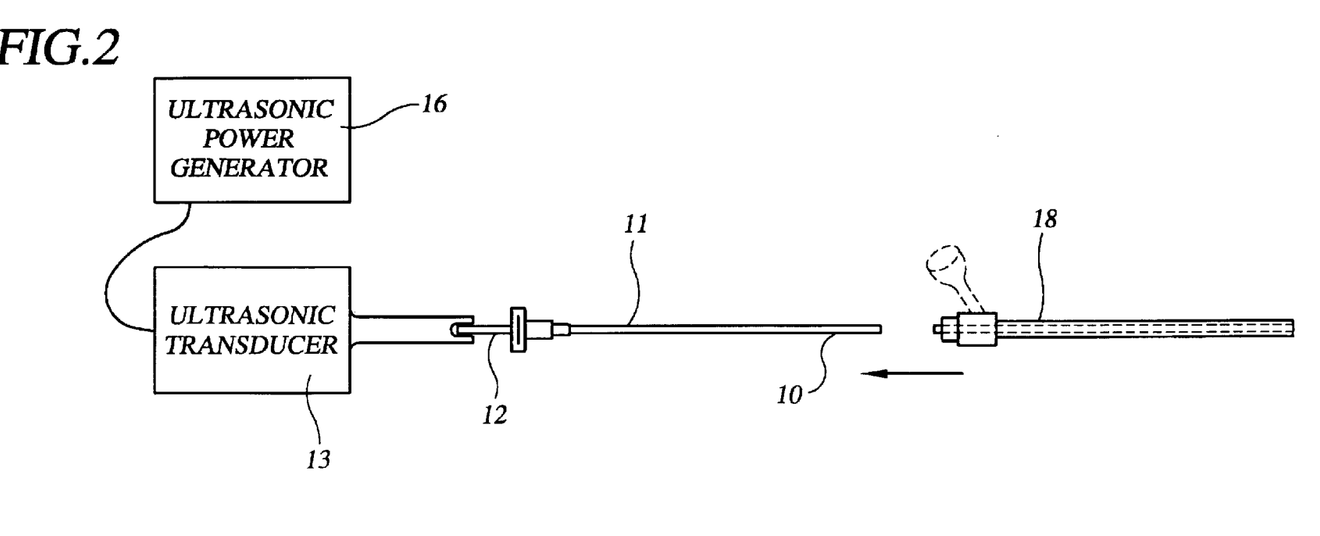
FIG. 2 is a longitudinal view of the ultrasonic resonator and generator with the resonator positioned within the interior channel of a rigid or flexible endoscope to be cleaned and having a "Y" connector assembled over the proximal region of the resonator.
Figure 3:
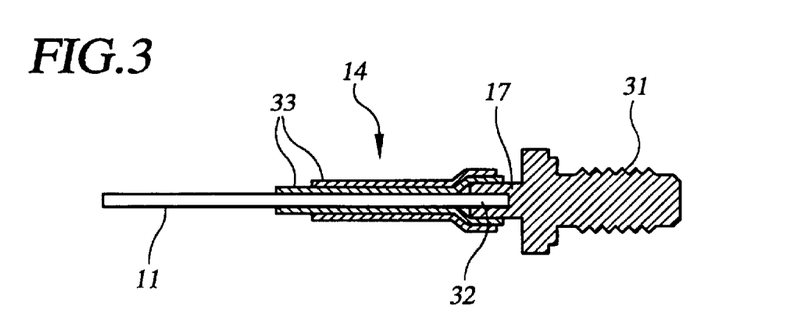
FIG. 3 is a sectional view of the proximal end of the ultrasonic resonator showing an embodiment of the coupling of the solid wire resonator to an ultrasonic transducer.

FIG. 2 is a longitudinal sectional view of the ultrasonic resonator (11) attached at its proximal end (12) to the ultrasonic transducer (13), which, in turn, is shown connected to an ultrasonic power generator (16). The resonator (11) is shown positioned in axial alignment with the instrument (18) to be cleaned. The solid resonator (11) is attached at the proximal end (12) to the tip of the ultrasonic transducer (13) by crimp screw (14) as depicted in FIG. 3. Crimp screw (14) is provided with threads (31) at one end and a hole (32) at the other end (17). The hole (32) is adapted to receive the proximal end of resonator (11). When the proximal end of resonator (11) is positioned in hole (32), the end (17) of the crimp screw (14) is crimped to provide a pressure attachment. The threaded end of the crimp screw (14) may be conveniently screwed into a compatible threaded opening in the transducer horn (not shown).

FIG. 3 further shows two layers of plastic tubing (33) which may, for example, be of Teflon to provide protection and to attenuate the ultrasonic energy at the attachment site, reducing the possibility of failure at the attachment site.

Figure 4:
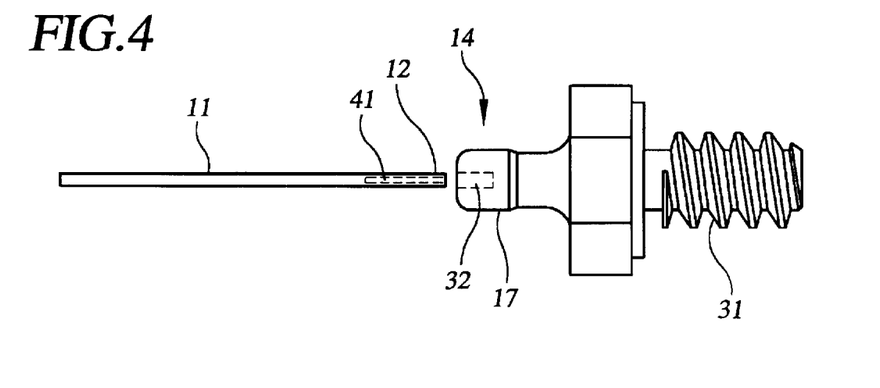
FIG. 4 is a sectional view of the proximal end of the ultrasonic resonator showing an embodiment of the coupling of the annular wire resonator to an ultrasonic transducer.

FIG. 4 is a longitudinal sectional view of the solid ultrasonic resonator (11) which will be attached at the proximal end (12) to the crimp screw (14) which is provided with threads (31) at one end and a hole (32) at the other end. The hole (32) is adapted to receive the proximal end (12) of resonator (11). When the proximate end (12) of resonator (11) is positioned in hole (32), the end (17) of the crimp screw (14) is crimped to provide a pressure attachment. FIG. 4 also depicts the location of the edm hole (41) and the solid ultrasonic resonator (11) before insertion into the crimp screw (14).

Figure 5:
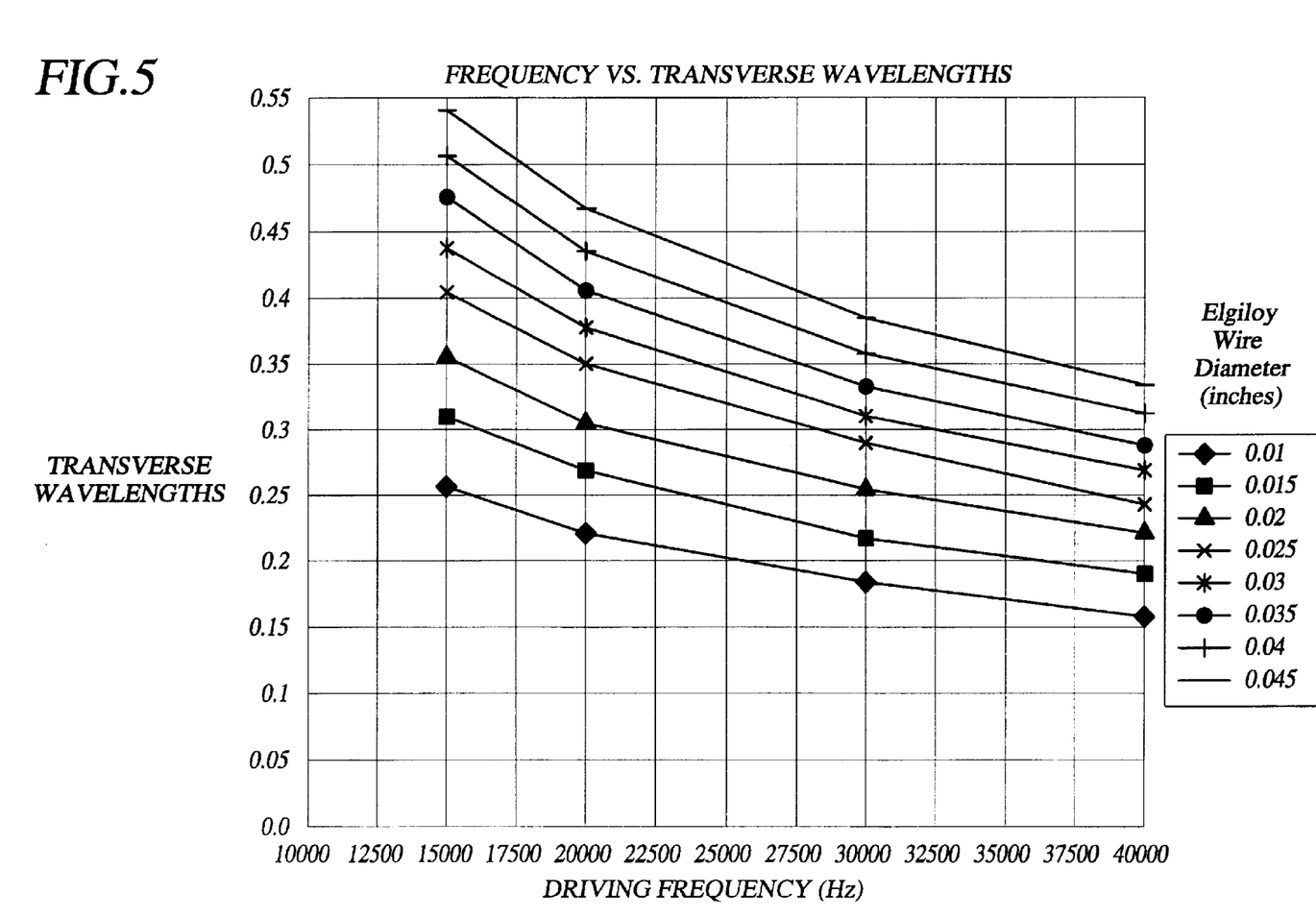
FIG. 5 is a plot of driving frequency and transverse wave lengths for various wire diameters.

The relationship between the operating or driving frequency and the transverse wavelength for wires of a given material and various diameters is shown in FIG. 5. In the chart, transverse wavelength (in inches) is plotted against driving frequency (Hz) for various diameters of Elgiloy wire. The Elgiloy wire employed was 48% cold reduced and heat treated at 980° F. for approximately five hours.

Figure 6:
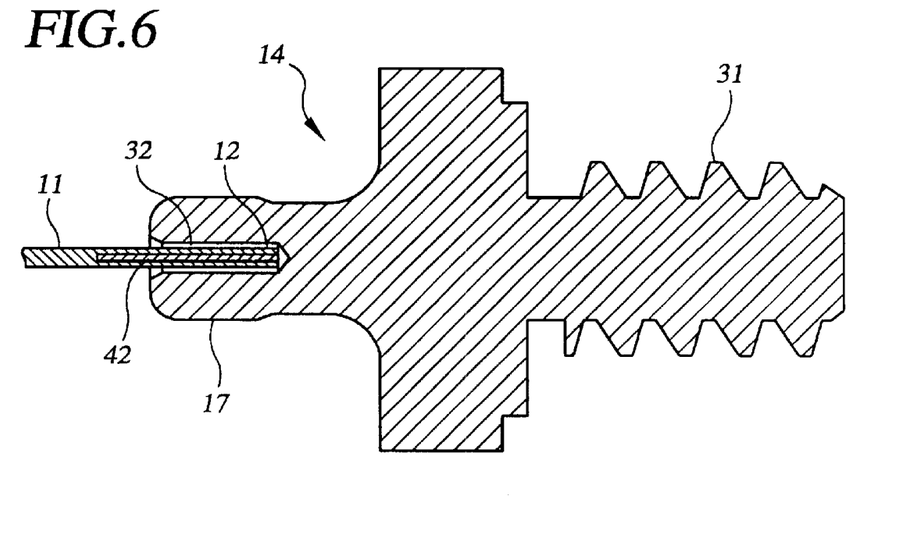
FIG. 6 depicts an overall view of the crimp screw, which attaches to the ultrasonic transducer, and the solid metal wire resonator with a filled edm hole before the screw is crimped.
Figure 7:
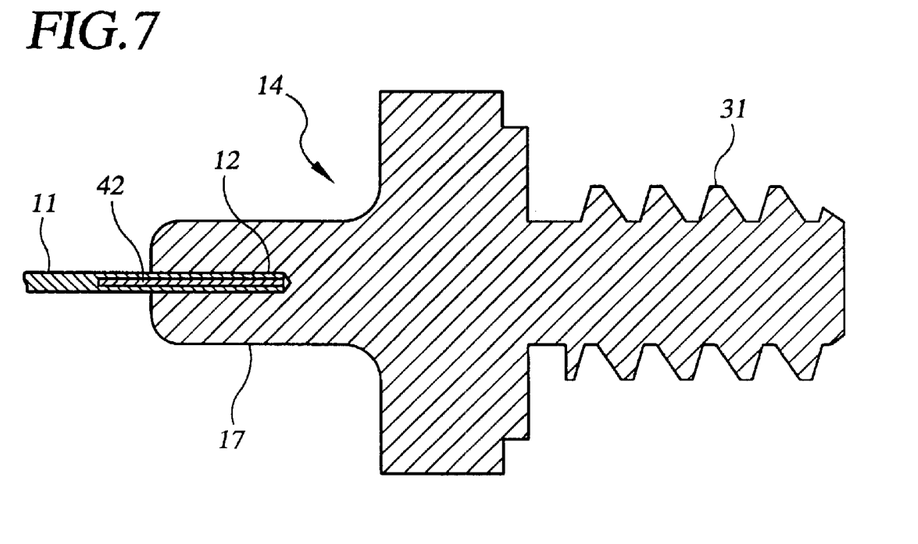
FIG. 7 depicts an overall view of the crimp screw, which attaches to the ultrasonic transducer, and the solid metal wire resonator with a filled edm hole after the screw is crimped.
Figure 8:
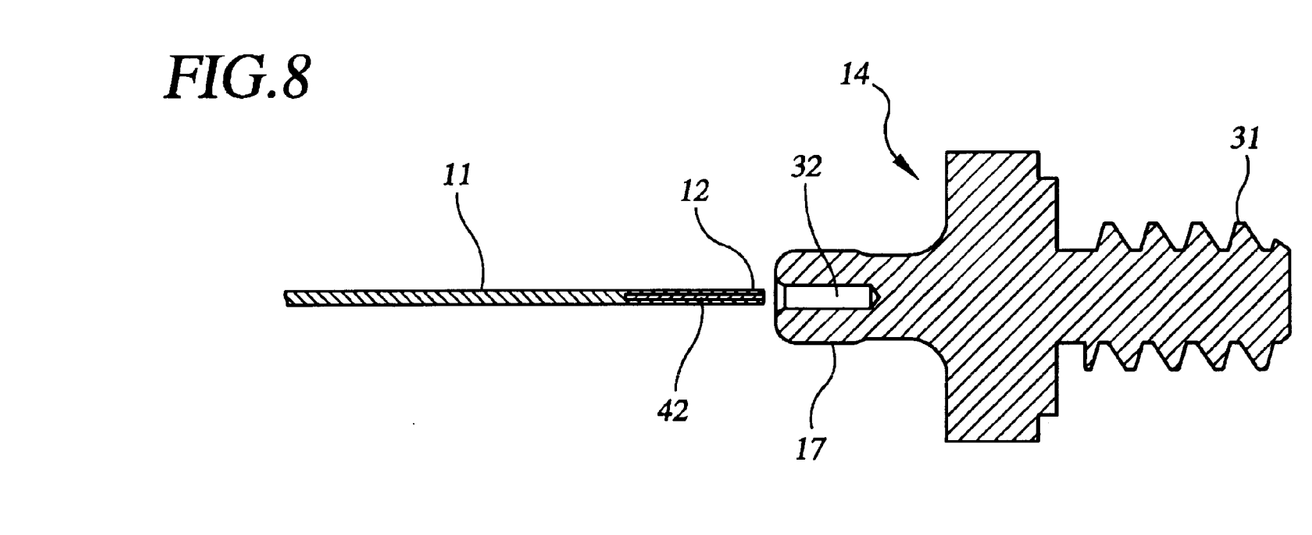
FIG. 8 depicts an overall view of the crimp screw and the solid metal wire resonator with filled edm hole before insertion into the screw.

FIG. 6 shows the solid resonator (11) with an edm hole (not numbered) contained within the proximal end (12) of the ultrasonic resonator (11) and inserted into the hole (32) of crimp screw (14) before crimping occurs. FIG. 6 also depicts the filler material (42) after insertion into the edm hole and the spatial relationship between the crimp screw (14) and the resonator (11). FIG. 7 shows the same elements as FIG. 6, but after crimping has occurred. FIG. 8 shows the same elements as FIG. 6, but before the resonator (11) is inserted into the crimp screw (14).

Figure 9A:
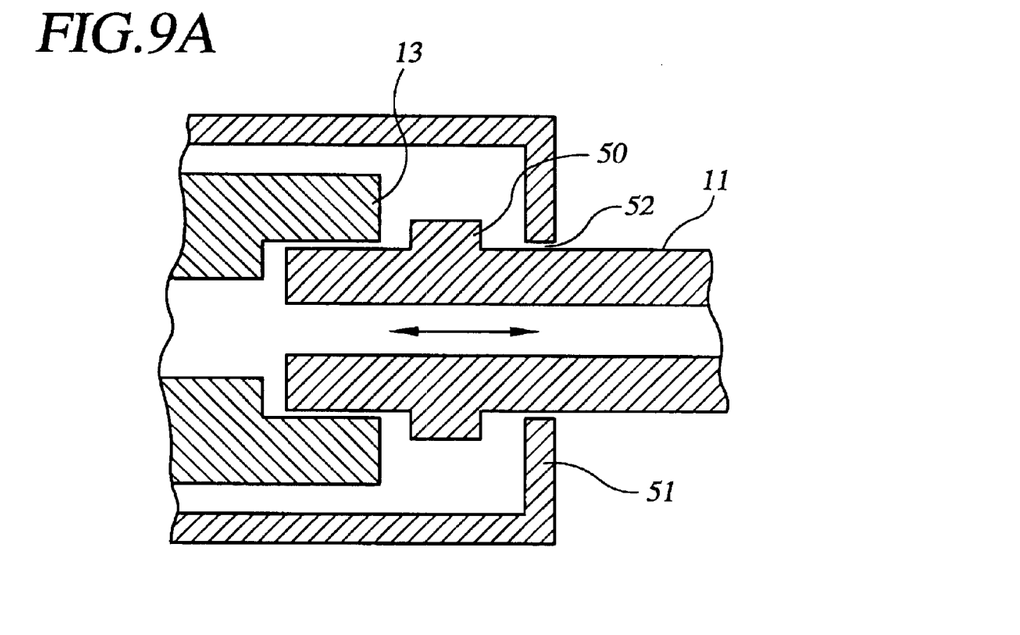
FIG. 9A is a sectional view of the coupling of an annular wire resonator to the ultrasonic transducer such that the wire resonator may move in a limited fashion.
Figure 9B:
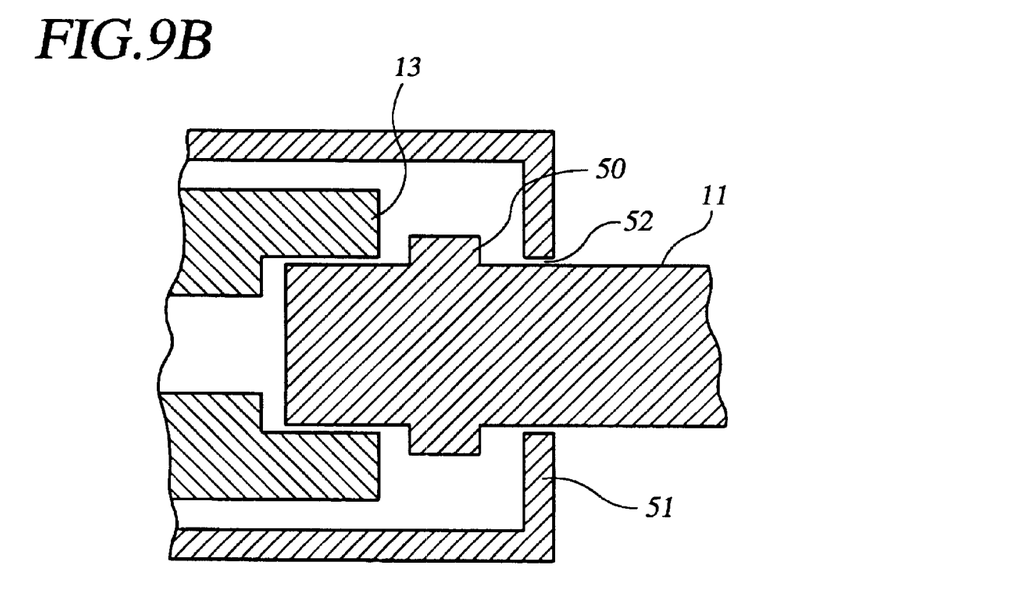
FIG. 9B is a sectional view of the coupling of a solid resonator to the ultrasonic transducer such that the wire resonator may move in a limited fashion.

FIGS. 9A and 9B depict an embodiment of this invention that allows for limited longitudinal movement of the resonator (11) with respect to the ultrasonic transducer (13). The wire resonator (11) can be annular as shown in FIG. 9A or solid as shown in FIG. 9B and is fitted with a capturing member (50) such that the capturing member (50) has opening (52) and is located a small distance from the proximal end of the resonator (11). The capturing member (50) may be shaped in many different ways, preferably the capturing member is an annular ring that fits over the resonator. A barrier member (51) is placed over the resonator (11) and the ultrasonic transducer (13) such that the capturing member (50) is located between the inner surface of the barrier member (51) and the tip of the ultrasonic transducer (13). This type of attachment is referred to as a "floating attachment" and allows the jackhammer-like movement of resonator (11).

Figure 10:
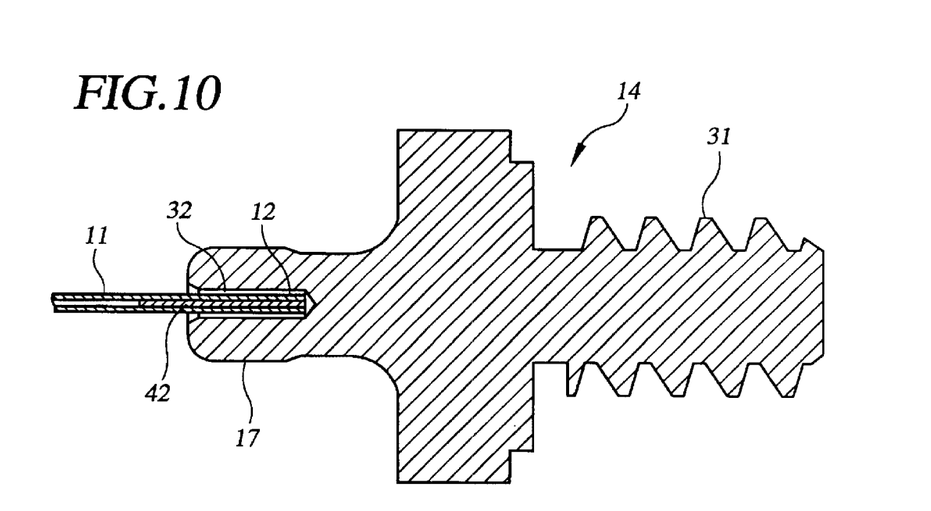
FIG. 10 depicts an overall view of the crimp screw, which attaches to the ultrasonic transducer, and the annular resonator and the filler material before the screw is crimped.
Figure 11:
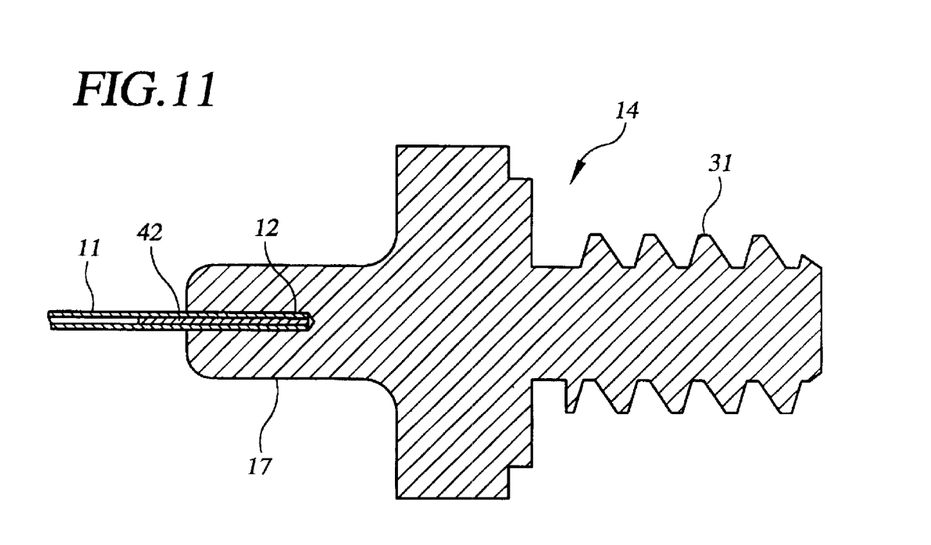
FIG. 11 depicts an overall view of the crimp screw, which attaches to the ultrasonic transducer, and the annular resonator and the filler material after the screw is crimped.
Figure 12:
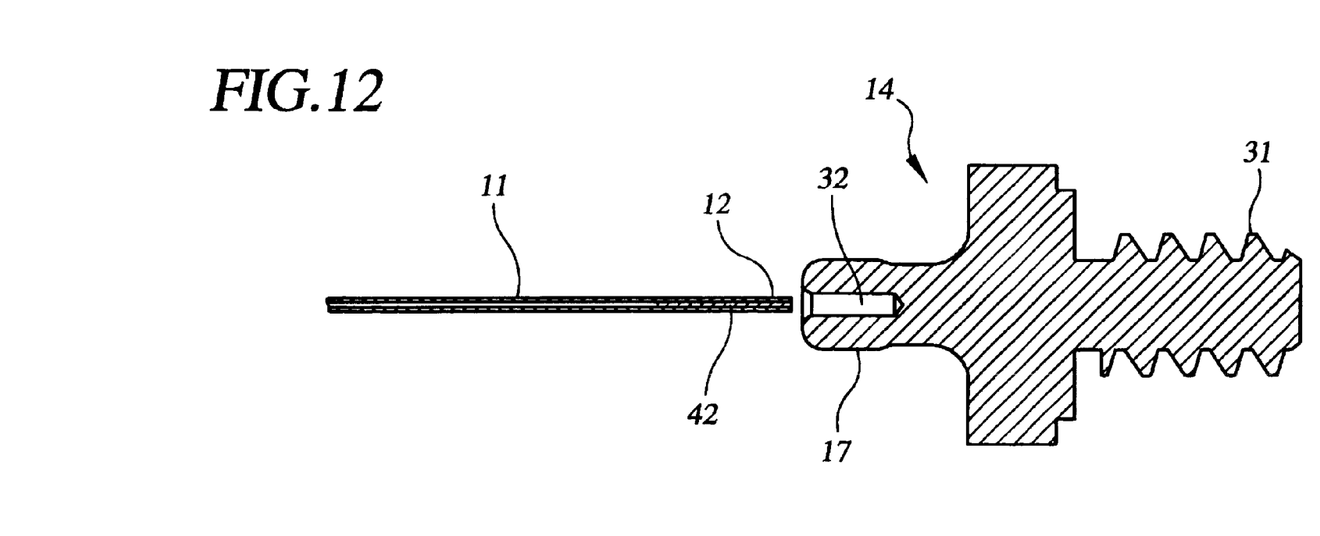
FIG. 12 depicts an overall view of the crimp screw and the annular resonator and the filler material before insertion into the screw.

Much like FIG. 6, FIG. 10 shows resonator (11) placed within crimp screw (14) before crimping, but with an annular resonator (11). FIG. 10 also depicts the filler material (42) after insertion into edm hole (not numbered) of annular resonator and the spatial relationship between the crimp screw (14) and the resonator (11). FIG. 11 shows the same elements as FIG. 10, but after crimping. FIG. 12 shows the same elements as FIGS. 10 and 11, but before the annular resonator (11) is inserted into the crimp screw (14).

Figure 14A:
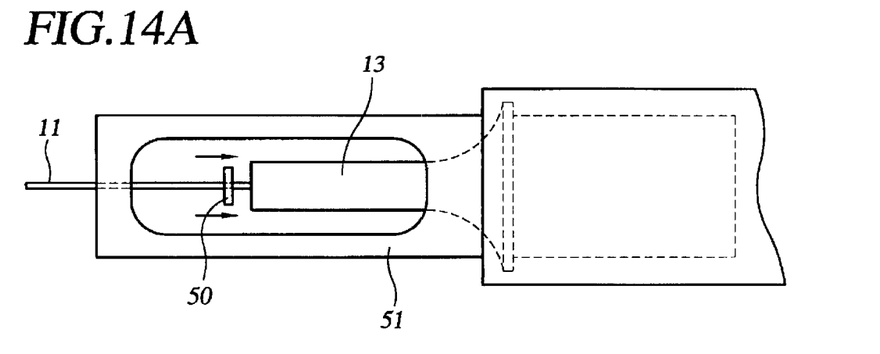
FIGS. 14A, 14B, and 14C depict the motion of the ultrasonic resonator that is coupled to the ultrasonic transducer such that the resonator may move in a limited fashion.
Figure 14B:
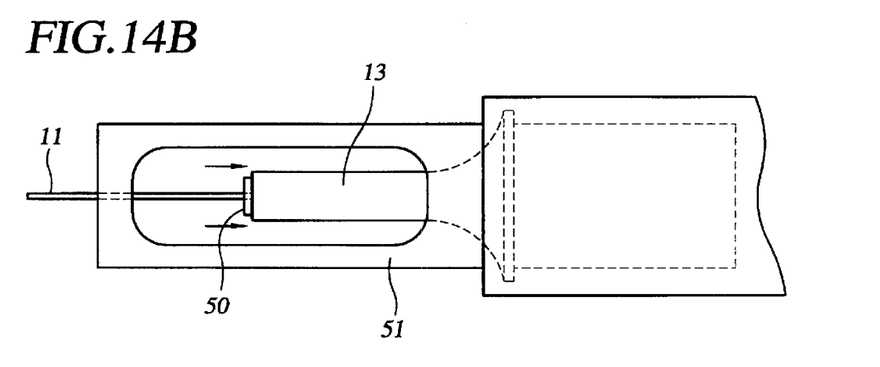
Figure 14C:
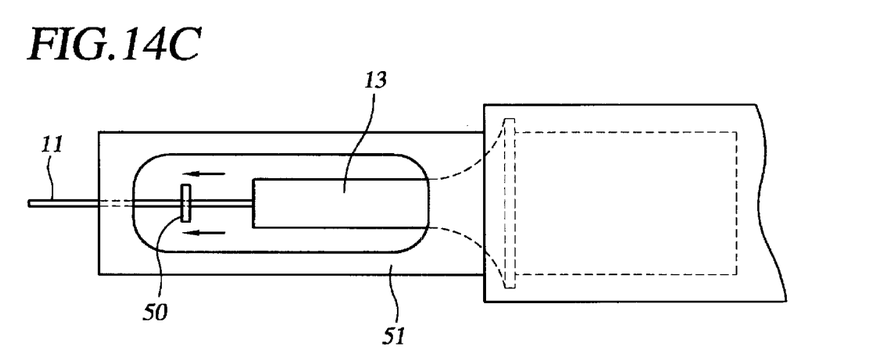

FIGS. 14A, 14B, and 14C depict the motion of the floating attachment through certain stages of the resonator's (11) motion.

Although, for convenience, the method and apparatus of the present invention have been described hereinabove primarily with respect to the cleaning of instruments as well as a few other applications, it will be apparent to those skilled in the art that the invention can be used for many other applications. Some of those applications are: cleaning ceramic investment castings; cleaning brain shunts; extraction of pacemaker and other leads from a human body; coring (including taking samples); drilling; and treating atherosclerotic plaque and thromboses.

We claim:

1. An ultrasonic resonator comprising:
   a wire member, said wire member having an elongated shaft with a proximal end and a distal end, said proximal end further including a filler material disposed within said proximal end;
   a crimp screw with an annular end and a threaded end, said annular end adapted to receive and fixedly secure said proximal end of said wire member, said annular end being crimped after said proximal end of said wire member is inserted within said annular end of said crimp screw, creating an attachment site; and
   an ultrasonic transducer adapted to receive said threaded end of said crimp screw.

2. The ultrasonic resonator of claim 1, further including an ultrasonic generator operatively connected to said ultrasonic transducer for driving said ultrasonic transducer.

3. The ultrasonic resonator of claim 1, wherein said ultrasonic resonator simultaneously produces both longitudinal ultrasonic vibrations and transverse ultrasonic vibrations, wherein said transverse ultrasonic vibrations occur at a plurality of antinode positions along said wire member.

4. The ultrasonic resonator of claim 1, wherein said wire member is constructed of a material selected from a group comprising nickel alloys, nickel-titanium alloys, titanium alloys, nickel-cobalt-chrome-molybdenum alloys, MP-35N alloy, Elgiloy, stainless steel, or plastic.

5. The ultrasonic resonator of claim 1, wherein said wire member is constructed of a material with a modulus of elasticity of at least approximately 18 million p.s.i.

6. The ultrasonic resonator of claim 1, wherein said wire member includes a protective coating.

7. The ultrasonic resonator of claim 6, wherein said protective coating is selected from a group comprising titanium nitride and polytetrafluoroethylene.

8. The ultrasonic resonator of claim 1, wherein said filler material is piano wire.

9. The ultrasonic resonator of claim 1, wherein said attachment site further includes two protective layers of a plastic tubing at said attachment site.

10. The ultrasonic resonator of claim 1, wherein said ultrasonic transducer is constructed of a plurality of piezoelectric elements, at least one metal separator, a horn, and a bias bolt, wherein each of said plurality of piezoelectric elements alternate with said at least one metal separator, a first piezoelectric element of said plurality of piezoelectric elements adjacent to said horn and a second piezoelectric element of said plurality of piezoelectric elements adjacent to said bias bolt, said bias bolt compressing said plurality of piezoelectric elements and said at least one metal separator against said horn.

11. The ultrasonic resonator of claim 10, wherein said ultrasonic transducer further includes at least one electric wire and at least one metal connector, wherein an ultrasonic generator is electrically connected to each of said at least one metal separator by one of said at least one electric wire via one of said at least one metal connector.

12. The ultrasonic resonator of claim 10, wherein each of said plurality of piezoelectric elements are made of a material selected from a group comprising a piezoelectric ceramic, a magnetostrictive material, a PZT 8 material, and a PZT 4 material.

13. The ultrasonic resonator of claim 1, wherein said wire member is annular.

14. The ultrasonic resonator of claim 1, wherein said wire member is solid, said wire member further including an edm hole at said proximal end formed by an electo-deposition materials process and adapted to receive said filler material.

15. The ultrasonic resonator of claim 14, wherein said edm hole has a maximum depth of about 0.1 inches.

16. The ultrasonic resonator of claim 1 further including a floating attachment, said floating attachment comprised of a capturing member and a barrier member adapted to direct said wire member in a limited back-and-forth longitudinal direction.

17. The ultrasonic resonator of claim 1, wherein said ultrasonic resonator operates in a pulsed mode to quickly degas a cleaning solution.

18. The ultrasonic resonator of claim 1, wherein said ultrasonic resonator is used in conjunction with a catheter assembly to introduce said ultrasonic resonator in vivo.

19. The ultrasonic resonator of claim 1, wherein said ultrasonic resonator is adapted for uses selected from a group comprising cleaning a medical device, cleaning an investment casting, cleaning a brain shunt, extracting a pacemaker lead, coring, drilling, treating atherosclerosis, and treating thrombuses.

20. An ultrasonic resonator comprising:
   an elongated wire member with a proximal end and a distal end, said proximal end containing a filler material disposed within said proximal end;
   a crimp screw with an annular end and a threaded end, said annular end adapted to receive and fixedly secure said proximal end of said elongated wire member, said annular end being crimped once said proximal end of said elongated wire member is inserted within said annular end of said crimp screw, creating an attachment site; and
   an ultrasonic transducer, said ultrasonic transducer constructed of a plurality of piezoelectric elements, at least one metal separator, a horn, and a bias bolt, said horn adapted to receive said threaded end of said crimp screw, each of said plurality of piezoelectric elements alternating with each of said at least one metal separator, a first piezoelectric element of said plurality of piezoelectric elements adjacent to said horn, and a second piezoelectric element of said plurality of piezoelectric elements adjacent to said bias bolt, said bias bolt compressing said plurality of piezoelectric elements and said at least one metal separator against said horn.

21. The ultrasonic resonator of claim 20, further including an ultrasonic generator operatively connected to said ultrasonic transducer for driving said ultrasonic transducer.

22. The ultrasonic resonator of claim 20, wherein said ultrasonic resonator simultaneously produces both longitudinal ultrasonic vibrations and transverse ultrasonic vibrations, wherein said transverse ultrasonic vibrations occur at a plurality of antinode positions along said elongated wire member.

23. The ultrasonic resonator of claim 20, wherein said elongated wire member is constructed of a material selected from a group comprising a nickel alloy, a nickel-titanium alloy, a titanium alloy, a nickel-cobalt-chrome-molybdenum alloy, an MP-35N alloy, an Elgiloy, a stainless steel, or a plastic.

24. The ultrasonic resonator of claim 20, wherein said elongated wire member is constructed of a material with a modulus of elasticity of at least approximately 18 million p.s.i.

25. The ultrasonic resonator of claim 20, wherein said wire member includes a protective coating.

26. The ultrasonic resonator of claim 25, wherein said protective coating is selected from a group comprising titanium nitrate and polytetrafluoroethylene.

27. The ultrasonic resonator of claim 20, wherein said filler material is piano wire.

28. The ultrasonic resonator of claim 20, wherein said attachment site further includes at least one layer of a plastic tubing at said attachment site to provide protection and to attenuate ultrasonic energy at the attachment site.

29. The ultrasonic resonator of claim 20, wherein said ultrasonic transducer further includes at least one electric wire and at least one metal connector, wherein an ultrasonic generator is electrically connected to each of said at least one metal separator by one of said at least one electric wire via one of said at least one metal connector.

30. The ultrasonic resonator of claim 20, wherein said piezoelectric elements are made of a material selected from a group comprising a piezoelectric ceramic, a magnetostrictive material, a PZT 8 material, and a PZT 4 material.

31. The ultrasonic resonator of claim 20, wherein said elongated wire member is annular.

32. The ultrasonic resonator of claim 20, wherein said elongated wire member is solid, said wire member further including an edm hole at said proximal end formed by an electo-deposition materials and adapted to receive said filler material.

33. The ultrasonic resonator of claim 32, wherein said edm hole has a maximum depth of about 0.1 inches.

34. The ultrasonic resonator of claim 20 further including a floating attachment, wherein said floating attachment is comprised of a capturing member and a barrier member adapted to direct said elongated wire member in a limited back-and-forth longitudinal direction.

35. The ultrasonic resonator of claim 20, wherein said ultrasonic resonator operates in a pulsed mode to quickly degas a cleaning solution.

36. The ultrasonic resonator of claim 20, wherein said ultrasonic resonator is used in conjunction with a catheter assembly to introduce said ultrasonic resonator in vivo.

37. The ultrasonic resonator of claim 20, wherein said ultrasonic resonator is adapted for uses selected from a group comprising cleaning a medical device, cleaning an investment casting, cleaning a brain shunt, extraction of a pacemaker lead, coring, drilling, treating atherosclerosis, and treating thrombuses.

38. A system comprising:
 a wire member, said wire member having an elongated shaft with a proximal end and a distal end, said proximal end containing a filler material, wherein said ultrasonic resonator simultaneously produces both longitudinal ultrasonic vibrations and transverse ultrasonic vibrations, said transverse ultrasonic vibrations occurring at a plurality of antinode positions along said wire member;
 a crimp screw with an annular end and a threaded end, said annular end adapted to receive and fixedly secure said proximal end of said wire member, said annular end being crimped once said proximal end of said wire member is inserted within said annular end of said crimp screw;
 an ultrasonic transducer adapted to receive said threaded end of said crimp screw; and
 an ultrasonic generator operatively connected to said ultrasonic transducer for driving said ultrasonic transducer.

39. The system of claim 38, wherein said wire member is constructed of a material selected from a group comprising nickel alloys, nickel-titanium alloys, titanium alloys, nickel-cobalt-chrome-molybdenum alloys, MP-35N alloy, Elgiloy, stainless steel, or plastic.

40. The system of claim 38, wherein said wire member is constructed of a material with a modulus of elasticity of at least approximately 18 million p.s.i.

41. The system of claim 38, wherein said wire member includes a protective coating.

42. The system of claim 41, wherein said protective coating is selected from a group comprising titanium nitride and polytetrafluoroethylene.

43. The system of claim 38, wherein said filler material is piano wire.

44. The system of claim 38, wherein said ultrasonic transducer is constructed of a plurality of piezoelectric elements, at least one metal separator, a horn, and a bias bolt, each of said plurality of piezoelectric elements alternating with said at least one metal separator, a first piezoelectric element of said plurality of piezoelectric elements adjacent to said horn, and a second piezoelectric element of said plurality of piezoelectric elements adjacent to said bias bolt, said bias bolt compressing said plurality of piezoelectric elements and said at least one metal separator against said horn.

45. The system of claim 38, wherein said ultrasonic transducer further includes at least one electric wire and at least one metal connector, wherein an ultrasonic generator is electrically connected to each of said at least one metal separator by one of said at least one electric wire via one of said at least one metal connector.

46. The system of claim 38, wherein said piezoelectric elements are made of a material selected from a group comprising a piezoelectric ceramic, a magnetostrictive material, a PZT 8 material, and a PZT 4 material.

47. The system of claim 38, wherein said wire member is annular.

48. The system of claim 38, wherein said wire member is solid, said wire member further including an edm hole at said proximal end formed by an electo-deposition materials process and adapted to receive said filler material.

49. The system of claim 48, wherein said edm hole has a maximum depth of about 0.1 inches.

50. The system of claim 38 further including a floating attachment, floating attachment comprised of a capturing member and a barrier member adapted to minimize transverse movement of said wire member and direct said wire member in a limited back-and-forth longitudinal direction.

51. The system of claim 38, wherein said ultrasonic resonator operates in a pulsed mode to quickly degas a cleaning solution.

52. The system of claim 38, wherein said ultrasonic resonator is used in conjunction with a catheter assembly to introduce said ultrasonic resonator in vivo.

53. The system of claim 38, wherein said ultrasonic resonator is adapted for uses selected from a group comprising cleaning a medical device, cleaning an investment casting, cleaning a brain shunt, extraction of a pacemaker lead, coring, drilling, treating atherosclerosis, and treating thrombuses.

* * * * *